(12) United States Patent
Colón et al.

(10) Patent No.: US 7,393,443 B2
(45) Date of Patent: Jul. 1, 2008

(54) METHODS OF IDENTIFYING KINETICALLY STABLE PROTEINS

(75) Inventors: Wilfredo Colón, Cohoes, NY (US); Marta Manning, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 253 days.

(21) Appl. No.: 10/924,235

(22) Filed: Aug. 23, 2004

(65) Prior Publication Data

US 2005/0069957 A1    Mar. 31, 2005

Related U.S. Application Data

(60) Provisional application No. 60/496,778, filed on Aug. 21, 2003.

(51) Int. Cl.
*B01D 59/42* (2006.01)
*G01N 31/00* (2006.01)

(52) U.S. Cl. ............................ 204/456; 436/2
(58) Field of Classification Search ...................... None
See application file for complete search history.

(56) References Cited

U.S. PATENT DOCUMENTS

| | | | |
|---|---|---|---|
| 5,360,729 | A | 11/1994 | Bartfeld et al. |
| 5,681,711 | A | 10/1997 | Bredesen |
| 5,710,033 | A | 1/1998 | Hallewell et al. |
| 5,843,641 | A | 12/1998 | Brown et al. |
| 6,331,421 | B1 | 12/2001 | Hallewell et al. |
| 2002/0164635 | A1 | 11/2002 | Salerno |
| 2004/0219570 | A1 | 11/2004 | Salerno |

OTHER PUBLICATIONS

Fasshauer et al. Structural Changes are Associated With Soluble N-Ethylmaleimide-Sensitive Fusion Protein Attachment Protein Receptor Complex Formation; The Journal of Biological Chemistry, vol. 272, No. 44 (1997) pp. 28036-28041.*
Stoll et al. Protein Microarray Technology; Frontiers in Bioscience, vol. 7, c13-32 (2002).*
Jin et al. Dynamic Labeling During Capillary or Microchip Electrophoresis for Laser-Induced Fluorescence Detection of Protein-SDS Complexes Without Pre or Postcolumn Labeling; Analytical Chemistry, vol. 73, No. 20 (2001) pp. 4994-4999.*
Fasshauer et al. Snare Assembly and Disassembly Exhibit a Promouned Hysteresis; Nature Structural Biology, vol. 9. No. 2 (2002) pp. 144-151.*
Jin et al. Dynamic Labeling During Capillary or Microchip Electrophoresis for Laser-Induced Fluorescence Detection of Protein-SDS Complexes Without Pre or Postcolumn Labeling; Analytical Biochemistry, vol. 73, No. 20 (2001) pp. 4994-4999.*
Shusta et al. Yeast Surface Display for Directed Evolution of Protein Expression, Affinity, and Stability; Methods in Enzymology, vol. 328 (2000) pp. 430-444.*
Nelson, C. The Binding of Detergents to Proteins; The Journal of Biological Chemistry, vol. 246, No. 12 (1971) pp. 3895-3901.*
Radunović, A. et al., "Cu/Zn Superoxide Dismutase Gene Mutations in Amyotrophic Lateral Sclerosis: Correlation Between Genotype and Clinical Features," *J. Neurology, Neurosurgery, and Psychiatry*, 61: 565-572 (1996).
Juneja, T. et al., "Prognosis in Familial Amyotrophic Lateral Sclerosis: Progression and Survival in Patients with Glu100gly and Ala4val Mutations in Cu, Zn, Superoxide Dismutase," *Neurology*, 48(1): 55-57 (1997).
Cudkowicz, M.E., et al., "Epidemiology of Mutations in Superoxide Dismutase in Amyotrophic Lateral Sclerosis," *Ann. Neuro.*, 41: 210-221 (1997).
Subramaniam, Jamuna R., et al., "Mutant SOD1 Causes Motor Neuron Disease Independent of Copper Chaperone-Mediated Copper Loading," *Nat. Neurosci.*, 5(4): 301-307 (2002).
Beckman, J.S., et al., "CCS Knockout Mice Establish an Alternative Source of Copper for SOD in ALS," *Free Radic. Biol. & Med.*, 33(10): 1433-1435 (2002).
Bush, A.I., "Is ALS Caused by an Altered Oxidative Activity of Mutant Superoxide Dismutase," *Nat. Neurosci.*, 5(10): 919-920 (2002).
"Drug Development and Clinical Trials: Drug Development Updates," retrieved from the Internet on Apr. 18, 2003. <http://alsa.org/research/drugdev.cfm>.

(Continued)

*Primary Examiner*—Jon P Weber
*Assistant Examiner*—Paul C. Martin
(74) *Attorney, Agent, or Firm*—Elmore Patent Law Group, P.C.; Darlene A. Vanstone; Carolyn S. Elmore (57) ABSTRACT

The present invention provides a fast and efficient means for identifying kinetically stable proteins. As used herein the term "kinetically stable protein" means a protein that is trapped in a specific conformation due to an unusually high unfolding barrier that results in very slow unfolding rates. The present inventors are the first to discover the existence of a correlation between kinetic stability and SDS-induced denaturation. Thus, the invention provides methods for identifying kinetically stable proteins comprising the step of testing the proteins for resistance to denaturation by SDS. In one embodiment, SDS-polyacrylamide gel electrophoresis (SDS-PAGE) is one simple method for quickly identifying and selecting kinetically stable proteins.

9 Claims, 6 Drawing Sheets

OTHER PUBLICATIONS

Morrison, Karen E., "Therapies in Amyotrophic Lateral Sclerosis-Beyond Riluzole," *Current Opinion in Pharmacology*, 2: 302-309 (2002).

Hardy, John and Gwinn-Hardy, Katrina, "Neurodegenerative Disease: A Different View of Diagnosis," *Molecular Medicine Today*, 5: 514-517 (1999).

Mathisen, Peter M., "Gene Discovery and Validation for Neurodegenerative Diseases," *DDT*, 8(1): 39-46 (2003).

Wang, Limin, et al., "Murine Apolipoprotein Serum Amyloid A in Solution Forms a Hexamer Containing a Central Channel," *PNAS*, 99(25): 15947-15952 (2002).

Cunningham, E.L., et al., "Kinetic Stability as a Mechanism for Protease Longevity," *Proc. Natl. Acad. Sci. USA*, 96: 11008-11014 (1999).

Ohnishi, S. And Kameyama, K., "*Escherichia coli* OmpA Retains a Folded Structure in the Presence of Sodium Dodecyl Sulfate Due to a High Kinetic Barrier to Unfolding," *Biochim. Biophys. Acta*, 1515: 159-166 (2001).

Kaushik, J.K., et al., The Unusually Slow Relaxation Kinetics of the Folding-Unfolding of Pyrrolidone Carboxyl Peptidase from a Hyperthermophile, Pyrococcus Furiosus, *J. Mol. Biol.*, 316: 991-1003 (2002).

* cited by examiner

PRIOR ART

METHODS OF IDENTIFYING KINETICALLY STABLE PROTEINS

RELATED APPLICATION

This application claims the benefit of U.S. Provisional Application No. 60/496,778, filed on Aug. 21, 2003. The entire teachings of the above application are incorporated herein by reference.

GOVERNMENT SUPPORT

The invention was supported, in whole or in part, by a grant, NSF MCB-9984913, from the National Science Foundation. The Government has certain rights in the invention.

BACKGROUND OF THE INVENTION

Figure 1:
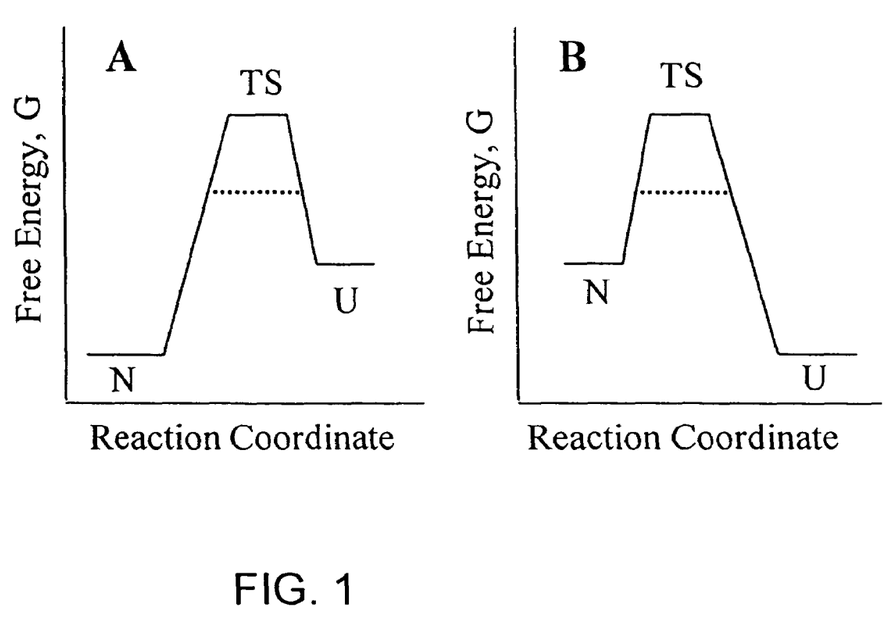
FIG. 1 is a free energy diagram to illustrate the higher unfolding energy barrier for a kinetically stable protein under native (A) and denaturing (B) conditions as compared to that of a normal protein (represented by the dash line).

Kinetic stability is a poorly understood property of a select group of naturally occurring proteins that are trapped in their native conformations by an energy barrier, and consequently are resistant to unfolding. Kinetic stability can be best explained by illustrating the unfolding process as a simple equilibrium reaction between two protein conformations, the native folded state (N) and the unfolded state (U), separated by a higher energy transition state (TS) (FIG. 1). Since the height of the TS barrier determines the rate of folding and unfolding, kinetically stable proteins possess an unusually high energy TS, which results in extremely slow unfolding rates that virtually trap the protein in its native state (FIG. 1A). Even though the overall change in Gibbs free energy ($\Delta G$) may be favorable for unfolding under extreme solvent conditions, such as high concentrations of denaturant, the high activation energy of the TS significantly slows down the unfolding rate (FIG. 1B). It has been suggested that the presence of a high kinetic energy barrier separating the folded and unfolded states is an evolutionary feature intended to allow proteins to maintain activity in the extreme conditions they may encounter in vivo (1). The examples of the kinetically stable proteins α-lytic protease (extracellular enzyme) (1), *Escherichia coli* OmpA (bacterial membrane protein) (2), and pyrrolidone carboxyl peptidase (hyperthermophilic protein) (3), illustrate the kinetic adaptation of proteins that must retain enzymatic function in conditions where degradation might easily take place. In addition, thermodynamic stability alone does not fully protect proteins that are susceptible to irreversible denaturation and aggregation arising from partially denatured states that become transiently populated under physiological conditions (4). Therefore, the development of a high kinetic energy barrier to unfolding may serve to protect susceptible proteins against such harmful conformational "side-effects".

The physical basis for kinetic stability is poorly understood and no structural consensus has been found to explain this phenomenon. In previous studies, the addition of hydrophobic residues on the protein surface (5), the engineering of disulfide bonds (6), and the introduction of metal-binding sites (7) have been shown to increase kinetic stability. A connection between kinetic stability and oligomeric quaternary structure has also been proposed (8). In the case of some hyperthermophilic proteins, electrostatic interactions have been suggested to be a major factor in their slow unfolding due to the formation of ion pairs (9, 10). However, there is evidence that some kinetically stable proteins retain their slow unfolding rate even at low pH, where electrostatic interactions should be significantly weakened (3, 11). Thus, it appears that no common structural feature exists to explain kinetic stability, and perhaps this property may be achieved by different means, depending on the individual protein.

Under native conditions, kinetically stable proteins have limited access to partially and globally unfolded conformations (12). These properties impart a strong proteolytic resistance by reducing the occurrence of accessible conformations susceptible to proteolytic attack (12, 13). Some kinetically stable proteins have also been found to be resistant to denaturation by sodium dodecyl sulfate (SDS). Among them are the β-sheet proteins streptavidin (14), transthyretin (15), P22 tailspike protein (16), and the *e-coli* membrane protein, OmpA (2).

The ability to quickly and easily identify kinetically stable proteins would have a myriad of applications in the biotechnology industry, pharmaceutical industry, and in basic life science research.

SUMMARY OF THE INVENTION

The present invention provides a fast and efficient means for identifying kinetically stable proteins. As used herein the term "kinetically stable protein" means a protein that is trapped in a specific conformation due to an unusually high unfolding barrier that results in very slow unfolding rates. The present inventors are the first to discover the existence of a correlation between kinetic stability and SDS-induced denaturation. Thus, the invention provides methods for identifying kinetically stable proteins comprising the step of testing the proteins for resistance to denaturation by SDS. In one embodiment, SDS-polyacrylamide gel electrophoresis (SDS-PAGE) is one simple method for quickly identifying and selecting kinetically stable proteins. This method has the advantage that proteins can be easily tested for kinetic stability without having to carry out unfolding experiments. Also, only microgram amounts of sample are needed, and the method is potentially suitable for identifying kinetically stable proteins present in cell extracts without need for purification. From an application perspective, this assay has the potential of being adaptable for various high-throughput applications to enhance the kinetic stability of proteins of interest. This could lead to proteins with greater shelf life and/or decreased tendency to aggregate, consistent with the suggestion that the deterioration of an energy barrier between native and pathogenic states as a result of mutation may be a key factor in the misfolding and aggregation of some proteins linked to amyloid diseases (4, 18). Such protein misfolding diseases include but are not limited to Alzheimer's disease, Parkinsons, prior-related encephalopathies, amyotrophic lateral sclerosis, and type II diabetes.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

The following abbreviations are used herein: ADH, Yeast Alcohol Dehydrogenase; AVD, Avidin; B2M, Beta2-microglobulin; BLA, Bovine Alpha-Lactalbumin; ConA, Concanavalin A; CPAP, Chymopapain; GAPDH, Glyceraldehyde 3-phosphate Dehydrogenase; GdnHCl, guanidine hydrochloride; MW, molecular weight; PAP, Papain; PB, phosphate buffer; SAP, Serum Amyloid P; SDS-PAGE, sodium dodecyl sulfate-polyacrylamide gel electrophoresis; SOD, Copper/Zinc Superoxide Dismutase; SVD, Streptavidin; TSP, P22 Tailspike protein; TIM, Triosephosphate Isomerase from porcine muscle; TTR, Transthyretin; Tris, 2-amino-2-hydroxymethyl-1,3-propanediol.

The invention provides a method for identifying a kinetically stable protein comprising testing the protein for resistance to denaturation by SDS. In one embodiment SDS-PAGE is used to assay the protein's resistance to SDS denaturation. In another embodiment, kinetically stable proteins are identified by a method comprising the steps of:
 a) providing at least one pair of substantially identical protein samples;
 b) adding SDS to each protein sample;
 c) boiling only one of the protein samples of the pair of protein samples;
 d) conducting SDS-polyacrylamide gel electrophoresis on the pair of protein samples; and
 e) comparing the migration on the gel of proteins contained in the boiled protein sample to the migration on the gel of proteins contained in the unheated protein sample.

Proteins that migrate to the same location on the gel regardless of whether or not the sample was boiled are classified as not being stable to SDS and are therefore not kinetically stable. Proteins that exhibit a slower migration when the sample is not boiled are at least partially SDS resistant and are considered to be kinetically stable. As used herein the term "substantially identical protein samples" means that each of the protein samples are collected from the same or similar source such as from the same protein library, wherein it is likely that a high percentage of the same proteins are present in each sample of the protein sample pair.

In yet another embodiment, a fluorescence-based assay may be used to test a protein's resistance to SDS denaturation.

In one embodiment a fluorescence-based assay for measuring SDS resistance comprises the steps of: a) generating a library of proteins by a display methodology using a well plate format; b) contacting the library of displayed proteins with SDS; c) washing unbound SDS from the proteins; d) contacting the protein library with a fluorescent probe capable of binding to an SDS-protein complex; and e) determining the intensity of fluorescence in each well. Kinetically stable proteins will be identified by their lack of fluorescence. This is because only the proteins that bind SDS will be fluorescent and the intensity of fluoresence may be used to quantifiy the extent of kinetic stability.

Display methodologies are well known in the art and include phage display, yeast protein display, antibody display and bacterial display. Various methods of phage display are described in U.S. Pat. Nos. 5,223,409 and 6,057,098, incorporated herein by reference. Yeast protein display is described in Border and Withrop, *Nature Biotech.* 15:553 (1997).

One skilled in the art recognizes that there are a various protocols for determining a protein's resistance to SDS denaturation and that all such protocols are useful in the methods of the present invention.

In another aspect, the invention provides a method for assessing the kinetic stability of a protein comprising the steps of: a) subjecting the protein to denaturation by SDS; and b) testing the ability of the protein to partially or totally resist SDS denaturation. In accordance with this aspect of the invention, the testing step may be accomplished by an SDS-PAGE assay or a fluorescence-based assay as described above. When an SDS-PAGE assay is used to test a protein's ability to resist denaturation, those proteins that migrate differently between the heated and unheated samples are kinetically stable or at least partially kinetically stable. The unheated sample containing a kinetically stable protein will migrate more slowly than its boiled counterpart and will appear on the gel as a slower solid band or a slower smear (in the case of a partially kinetically stable protein).

In another aspect, the invention provides a method of identifying the presence of kinetically stable proteins in a library of proteins generated by any means, comprising the step of testing proteins in the protein library for resistance to denaturation by SDS. For example, either an SDS-PAGE assay or fluorescence-based assay, both as described above, may be used to identify kinetically stable proteins in the protein library. The methods of the invention are particularly useful in improving processes involving the manipulation and engineering of proteins by providing a rapid means for identifying kinetically stable proteins in the libraries of known proteins, random proteins, mutagenized proteins, chimeric proteins, fusion proteins, and chimeric fusion proteins often produced in the course of such protein manipulation or engineering.

A protein library may be the result of, for example, rational protein design, site-directed mutagenesis, directed evolution, protein genesis, and gene shuffling, or the protein library may be a combinatorial array of proteins. The present invention is particularly useful for high-throughput screening to identify kinetically stable proteins present in such protein libraries.

In one embodiment, the present invention is used as a high-throughput screen to identify kinetically stable chimeric polypeptides generated from a library of chimeric polynucleotides prepared in accordance with known techniques for producing libraries of chimeric polynucleotides and combinatorial chimeric polynucleotides (e.g. rational protein design, protein genesis, directed evolution, site-directed mutagenesis and gene shuffling). As used herein, a "polynucleotide" is a polymeric chain of nucleotides (e.g., a gene, gene fragment, cDNA, mRNA), and a "polypeptide" is a polymeric chain of amino acids (e.g., a protein). "Chimeric polynucleotides" are polynucleotides that contain regions derived from two or more parent genes as opposed to site-directed mutagenized DNA comprising only point mutations or insertion and deletion mutations ("indels"). Chimeric polynuceotides are useful in techniques such as "gene shuffling" (see, e.g. Crameri, A., et al., Nature 391 (6664):228-291 (1998)) and other processes aimed at engineering proteins with novel properties (see also U.S. Pat. No. 5,223,409).

The invention is particularly suited for application to the methods of generating, by directed evolution, chimeric polypeptides as described in copending U.S. application Ser. No. 10/712,806, filed on Nov. 13, 2003 and copending U.S. application Ser. No. 10/138,183, filed on May 2, 2003, both of which are incorporated herein by reference in their entirety. These applications pertain to methods for generating chimeric polynucleotides, such as polynucleotides encoding polypeptides ("chimeric polypeptides"), using directed evolution of a basis set of polynucleotides. A "basis set" is a group of 2 or more polynucleotides, preferably greater than or equal to 3 polynucleotides, such as between 3 and 12 polynucleotides, inclusive, or more; the basis set of polynucleotides is used as the starting materials for the directed evolution. The present invention is particularly useful in identifying kinetically stable chimeric polypeptides resulting from the directed evolution process described therein.

The invention is also suited for identifying kinetically stable proteins and polypeptides produced by the various methods described in the following patent applications: U.S. Provisional Patent Applications Nos.: 60/445,689, 60/445,704, 60/445,703 (all filed on Feb. 6, 2003) and 60/474,063 (filed on May 29, 2003), all incorporated herein by reference in their entirety. The methods described in these patent applications relate to generating libraries of chimeric oligonucleotides, combinatorial chimeric oligonucleotides and oligonucleotides having point mutations, insertions and deletions using polymerase-based procedures, for expression in a host cell. The resulting libraries of polypeptides and proteins may then be conveniently screened for kinetically stable proteins using the methods of the present inventions.

Thus the invention provides methods of identifying kinetically stable chimeric polypeptides produced from a library of chimeric polynucleotides generated by directed evolution comprising the steps of: a) generating a library of chimeric polynucleotides by directed evolution; b) expressing the library of chimeric polynucleotides in a host cell; and c) screening the resulting chimeric polypeptides for resistance to denaturation by SDS. In one embodiment, the screening step comprises assaying the chimeric polypeptides for resistance to denaturation by SDS using an SDS-PAGE assay. In another embodiment, the screening step comprises the steps of:
  a) providing at least one pair of substantially identical chimeric polypeptide samples derived from a chimeric polypeptide library, each sample comprising at least one polypeptide in combination with SDS;
  b) boiling only one of the chimeric polypeptide samples of the pair of samples;
  c) conducting SDS-polyacrylamide gel electrophoresis on the pair of chimeric polypeptide samples; and
  d) comparing the migration of polypeptides contained in the boiled chimeric polypeptide sample to the migration of polypeptides contained in the unheated chimeric polypeptide sample. In one embodiment, the method further comprises step d) identifying those proteins that migrate differently between the boiled and unheated samples as kinetically stable or partially kinetically stable. Kinetically stable polypeptides present in the cell extract of the host cells used to express the polypeptides can be identified using an SDS-PAGE assay without the need for further purification steps.

In addition to identifying chimeric polypeptides, the invention also provides methods for identifying kinetically stable mutated proteins in a library of mutated proteins generated by site-directed mutagenesis of polynucleotides (e.g. by insertions, deletions and point mutations of polynucleotides) In one embodiment, the invention provides a method for identifying kinetically stable mutated proteins in a library of mutated proteins produced by site-directed mutagenesis comprising the steps of:
  a) generating by site-directed mutagenesis, a library of mutated polynucleotides;
  b) expressing the library of mutated polynucleotides in host cells; and
  c) screening the resulting mutated polypeptides expressed in the host cells for resistance to denaturation by SDS. Any of the methods for testing a protein's resistance to SDS denaturation as described above are useful for screening the resulting mutated polypeptides expressed in the host cells for resistance to denaturation by SDS.

One skilled in the art will appreciate the many advantages that the method of the invention provides in addition to those described above. For example, the methods of the invention are useful in protein and enzyme engineering technologies (e.g. rational protein design, protein genesis, directed evolution, site-directed mutagenesis and gene shuffling) for the production of industrial proteins and enzymes such as detergent enzymes, enzymes useful for neutralizing contaminants and enzymes useful as fuel additives. Likewise, the methods of the invention are useful in protein engineering technologies for the production of proteins and enzymes useful in the food and life sciences industries such as primary and secondary metabolites useful in the production of antibiotics, proteins and enzymes for the food industry (bread, beer), and combinatorial arrays of proteins for use in generating multiple epitopes for vaccine production. The methods of the invention are also particularly useful in the design and development of diagnostics or therapeutics where protein stability is a desired or necessary characteristic of the diagnostic reagent or the embodiments in which the ability to quickly identify kinetically stable proteins in accordance with the invention is of particular use. A more specific discussion of a few of these many uses is included below for exemplary purposes. One skilled in the art can appreciate the many applications of this technology are not limited to those described herein.

In one embodiment, the methods of the invention are useful in conjunction with drug discovery. For example, in diseases characterized by protein misfolding and aberrant protein aggregation (see, Table 1 and associated references), novel compounds such as small molecules can be tested for their ability to impart kinetic stability to a protein that may otherwise misfold or aggregate. One example of a drug discovery method utilizing the methods of the invention comprises the steps of: a) providing a library of small molecules; b) probing the library with a protein prone to misfolding and/or aberrant aggregation; c) assaying the proteins complexes to which the small molecules have bound ("protein/small molecule complexes") for kinetic stability by testing the ability of the protein/small molecule complexes to resist denaturation by SDS. Resistance to SDS denaturation may be tested, for example, by using an SDS-PAGE assay or a fluorescence based assay. The small molecules that have imparted kinetic stability to a protein to which the small molecule has bound may serve as the basis for further investigation and drug development.

In yet another embodiment the methods of the invention are useful in conjunction with prophylactic or therapeutic

TABLE 1

Amyloid-Forming Proteins Known to be Associated with Disease

| Precursor Protein | Clinical Syndrome | Native Structure | Amyloidogenic species |
|---|---|---|---|
| β-protein | Alzheimer's disease | Little stable secondary structure | Aβ1-40, 1-42 |
| Serum Amyloid A | Secondary Systemic (AA) Amylodosis | Mixed alpha/beta | Full length, 1-76 |
| Transthyretin | Senile Systemic Amyloidosis; familial amyloid polyneuropathy | Mainly beta | Full length, fragments |
| Islet Amyloid Peptide (amylin) | Type II diabetes | Little stable secondary structure | Full length |
| Immunoglobulin Light Chain | Primary Systemic (light chain) Amyloidosis | | Full length, fragments |
| Apolipoprotien A-I | Familial Amyloid Polyneuropathy (III) | Mainly helix | Fragments |
| Atrial Natriuretic Factor | Atrial Amyloidosis | | |
| Gelsolin | Finnish Hereditary Systemic Amyloidosis | Mixed alpha/beta | 71 residue fragment |
| Cystatin C | Hereditary Cerebral Amyloid Angiopathy | | |
| β$_2$-microglobulin | Hemodialysis-related amyloidosis | | |
| Prion | Spongiform Encephallpathies | Mainly helix | Full length, fragments |
| Calcitonin | Medullary Carcinoma of the Thyriod | Little stable secondary structure (Central helix with turns) | Full length |
| Fibrinogen | Hereditary Renal amyloidosis | Mixed alpha/beta | Mutant form |
| Insulin | Injection-localized amyloidosis | Mainly helix | Full length |
| lactadherin | Aortic medial amyloid | unknown | Residues 245-294 (Medin) |
| Lysozyme | Hereditary non-neuropathic systemic amyloidosis | Mainly helix | Mutant form |
| α-Synuclein | Parkinson's disease | Little stable secondary structure | Mutant form |
| Tau Protein | Alzheimer's disease | Little stable secondary structure | |
| Superoxide Dismutase | FALS | Mainly beta | |
| bovine crystallins | Cataracts (?) | Mainly beta | |
| SH3 domain of the p85alpha subunit of bovine phosphatidylinositol 3'-kinase (PI3-SH3) | None known | Mainly beta | Full length |
| Huntington Protein | Huntington's Disease | | Polyglutamate (greater than 39) repeats |

In another embodiment, the methods of the invention are useful in conjunction with diagnostic procedures for identifying proteins that have an increased tendency to misfold and aggregate, resulting in diseases such as those listed in Table 1. The present invention is useful in quickly identifying proteins in specific cells (by culturing the cells), or in plasma, that have lost their stability due to mutation or other pathology associated with the disease. One exemplary diagnostic assay comprises the steps of: a) obtaining a protein sample from a patient known to contain a protein whose loss of kinetic stability leads to disease; b) assaying the protein sample for proteins resistant to SDS; and c) identifying proteins that are not resistant to denaturation by SDS. Those proteins that are not resistant to denaturation by SDS are not kinetically stable. The loss of kinetic stablility of a protein known to be associated with disease may be indicative of the onset or presence of the associated disease.

treatments of disease. In one example of this embodiment, diseases characterized by the onset or instability of certain proteins may be treated by administering to the patient a kinetically stable form of the same protein which may then be capable interact with defective protein and stabilize or prevent the unstable proteins from aberrant aggregation. Therefore, in one embodiment, diseases characterized by the instability of a protein associated with a disease are treated by administering to a patient in need thereof, a therapeutically effective amount of a kinetically stable form of the protein associated with the disease wherein the kinetically stable form of the protein was identified from a library of proteins known to be associated with the disease, by assaying the library for proteins that are resistant to SDS denaturation.

The present inventors are the first to discover the connection between the kinetic stability of a particular protein and its ability to resist denaturation by SDS. In order to investigate the relationship between kinetic stability and SDS resistance, over thirty proteins, including some known to be SDS resistant and/or kinetically stable, were studied (Table 2).

TABLE 2

List of Proteins that Were Analyzed by SDS-PAGE to Assay for SDS Resistance

| Protein | 2° Structure | No. of Subunits | SDS-stable? |
|---|---|---|---|
| alcohol dehydrogenase | mixed | 1 | no |
| avidin | beta | 2 | yes |
| beta amylase | alpha | 1 | no |
| carbonic anhydrase | mixed | 1 | no |
| catalase | alpha | 1 | no |
| chymopapain | mixed | 1 | yes |
| chymotrypsin | mixed | 2 | no |
| concanavalin A | beta | 2 | no |
| gamma crystallin | beta | 1 | no |
| beta glucoronidase | mixed | 2 | no |
| glyceraldehyde-3-phosphate dehydrogenase | alpha | 6 | no |
| hemocyanin | mixed | 6 | no |
| hemoglobin | alpha | 2 | no |
| hyaluronidase | alpha | 1 | no |
| insulin | mixed | 1 | no |
| alpha lactalbumin | mixed | 1 | no |
| luciferase | alpha | 2 | no |
| lysozyme | mixed | 1 | no |
| beta microglobulin | beta | 1 | no |
| neuraminidase | beta | 1 | no |
| papain | mixed | 1 | yes |
| P22 tailspike | beta | 3 | yes |
| pectin lyase A | beta | 2 | no |
| rhodanese | mixed | 1 | no |
| ribonuclease A | mixed | 1 | no |
| rubredoxin | beta | 1 | no |
| serum amyloid P | beta | 5 | yes |
| streptavidin | beta | 4 | yes |
| Cu/Zn superoxide dismutase | beta | 2 | yes |
| transthyretin | beta | 4 | yes |
| triose phosphate isomerase | alpha | 2 | no |
| trypsin | beta | 1 | no |
| urease | mixed | 2 | no |

Figure 2:
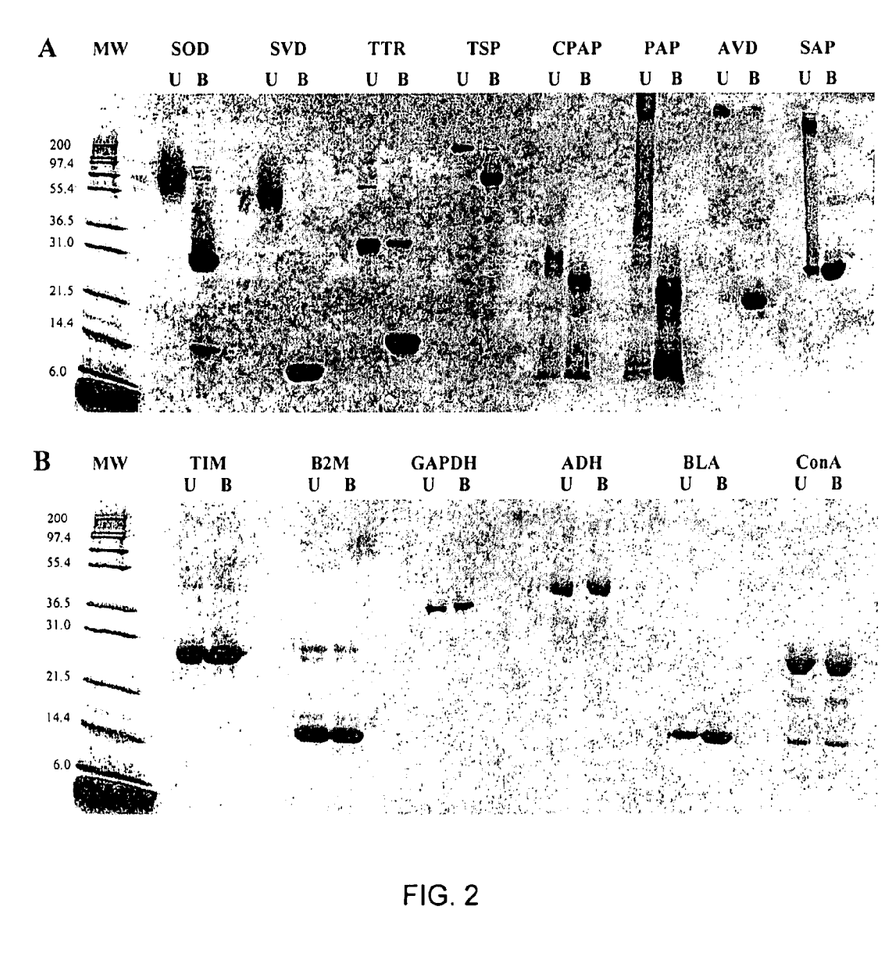
FIG. 2 is an SDS-PAGE assay of SDS-resistant proteins (A) and the non SDS-resistant control group (B). Identical protein samples were either unheated (U) or boiled (B) for 10 min immediately prior to loading onto the gel.

Among these were a few control proteins (streptavidin, transthyretin, and P22 tailspike) that were independently known to be both kinetically stable (via folding experiments) and SDS resistant. SDS resistance was assayed by comparing the migration on a gel of boiled and unboiled protein samples containing SDS (FIG. 2). Proteins that migrated to the same location on the gel regardless of whether or not the sample was boiled were classified as not being stable to SDS (FIG. 2B). Those proteins that exhibited a slower migration when the sample was not boiled were classified as being at least partially resistant to SDS-induced denaturation (FIG. 2A). The slower migration is a sign of decreased SDS binding, and consequently of a lesser overall negative charge of the SDS-protein complex compared to the fully SDS-bound proteins. Of the proteins tested, eight were found or confirmed to exhibit resistance to SDS, including Cu/Zn superoxide dismutase, streptavidin, transthyretin, P22 tailspike, chymopapain, papain, avidin, and serum amyloid P (Table 2, FIG. 2A).

Figure 3:
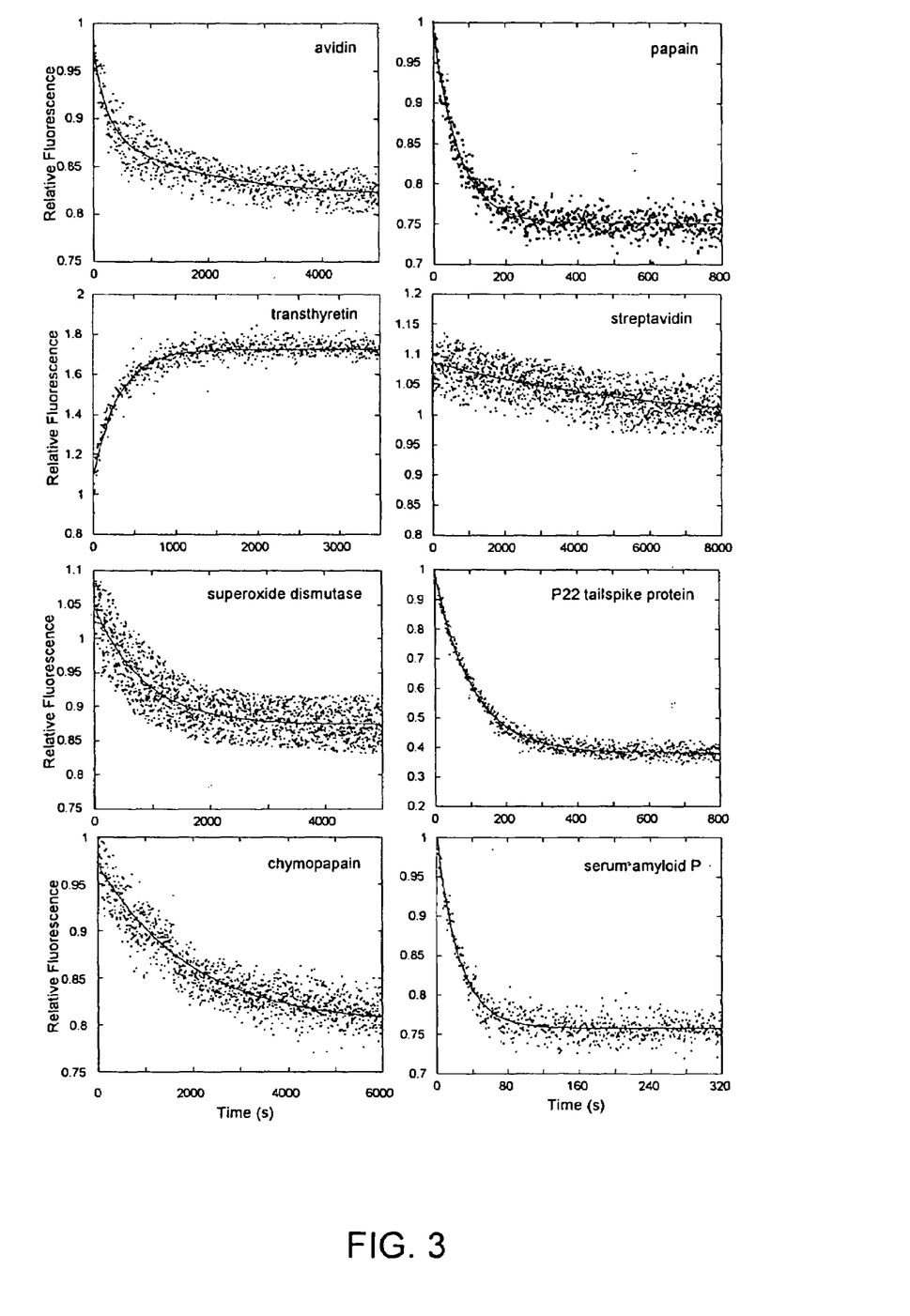
FIG. 3 shows fluorescence-detected unfolding kinetics of the SDS-resistant proteins upon incubation in 6.6 M guanidine hydrochloride (GdnHCl) at 20° C. Relative fluorescence was obtained by dividing each data point by the first point of the native protein baseline. No missing amplitude was observed, indicating that the observed kinetic trace accounts for the full unfolding transition.
Figure 4:
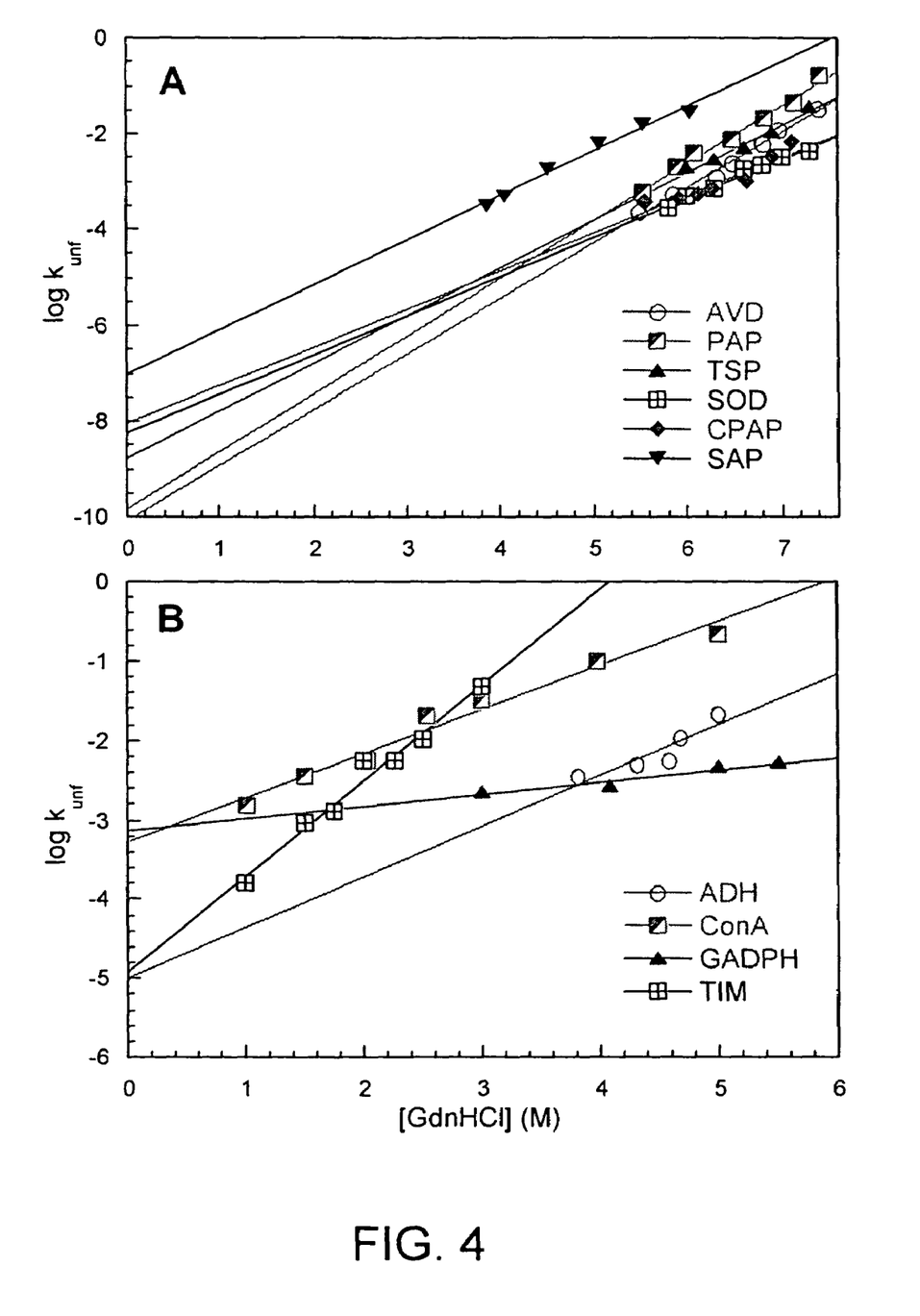
FIG. 4 shows the unfolding rate of the SDS-resistant (A) and non SDS-resistant control group (B) under native-like conditions shown by extrapolating the unfolding rate determined at different concentration of GdnHCl to 0 M. The y-intercept of each extrapolation curve indicates the native protein's unfolding rate (Table 2)

To probe the kinetic stability of the SDS-resistant proteins, fluorescence spectroscopy was used (FIG. 3) to demonstrate their slow unfolding rates even in 6.6 M GdnHCl at 20° C. To gather further evidence of the kinetic stability exhibited by these proteins under native conditions, their unfolding rate constants in the absence of denaturant were obtained by measuring the unfolding rate at different GdnHCl concentrations and extrapolating to 0 M (FIG. 4A). The native state unfolding rate constants for TTR (17) and SVD (14) were obtained from the literature. The unfolding rate in the absence of denaturants was found to be very slow (Table 2), with protein half-lives ranging from 79 days to 270 years. Thus, the fact that all the SDS-resistant proteins are also kinetically stable, suggest that the latter property may be responsible for the former.

To further test the correlation between kinetic stability and SDS resistance, a group of six proteins was selected that did not exhibit resistance to SDS and analyzed their unfolding behavior in varying concentrations of GdnHCl. The group was chosen to represent a variety of structural characteristics, and consisted of porcine triosephosphate isomerase (TIM), glyceraldehyde 3-phosphate dehydrogenase (GAPDH), beta2-microglobulin (B2M), bovine alpha-lactalbumin (BLA), concanavalin A (ConA), and yeast alcohol dehydrogenase (ADH). At 6.6 M, the unfolding of these proteins was too fast to detect with a standard fluorescence spectrophotometer (data not shown). The lack of kinetic stability exhibited by these proteins was further demonstrated by their native unfolding rates, which ranged from 14 min to 19 h (FIG. 4B, Table 2).

The results support the existence of a correlation between kinetic stability and resistance to SDS-induced denaturation. Therefore, SDS-PAGE serves as a simple method for identifying and selecting kinetically stable proteins. This method has the advantage that proteins can be easily tested for kinetic stability without having to carry out unfolding experiments. Also, only microgram amounts of sample are needed, and the method is potentially suitable for identifying kinetically stable proteins present in cell extracts without need for purification. From an application perspective, this assay has the potential of being adaptable for various high-throughput applications to enhance the kinetic stability of proteins of interest. This could lead to proteins with greater shelf life and/or decreased tendency to aggregate, consistent with the suggestion that the deterioration of an energy barrier between native and pathogenic states as a result of mutation may be a key factor in the misfolding and aggregation of some proteins linked to amyloid diseases (4, 18).

SDS is an anionic detergent, and is a strong denaturant of proteins when present at concentrations above its critical micelle concentration (~7 mM in water) (19, 20). Although there are examples in the literature of proteins that are not susceptible to denaturation by SDS, it is not clear what chemical-physical property is responsible for this resistance. It has been shown that there is no correlation between thermodynamic stability and SDS resistance (21). Although it has been suggested that surface charges in a protein can modulate SDS resistance, there is no general effect. For example, very acidic proteins, such as pepsin, will not interact with SDS because of charge repulsion (21). However, proteins with a high ratio of basic to acidic residues on the surface are not necessarily more susceptible to being denatured by SDS. The ratio of basic to acidic residues was calculated on the eight SDS resistant proteins in the study and a value of 1.2±0.2 was obtained, which is slightly higher than the ratio (0.95) that was calculated for the average protein based on amino acid composition.

Figure 5:
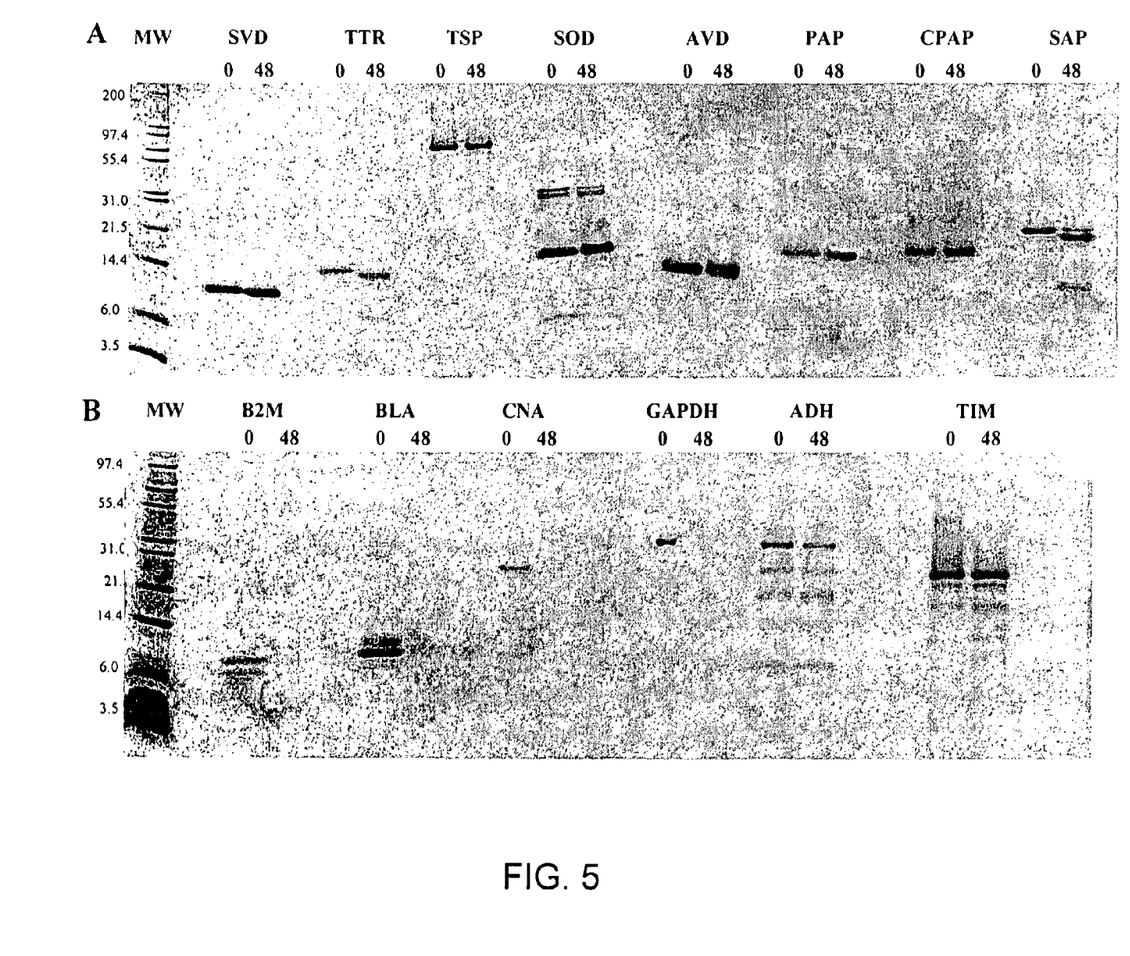
FIG. 5 shows the proteolytic resistance of the SDS-resistant proteins (A) and proteolytic susceptibility of the non-resistant control group (B) determined by incubating them for 48 hours with Proteinase K using a protease:protein ratio of 1:100 (w/w) and boiling the samples prior to loading onto the gel.

To explore the correlation between SDS-resistance and the structural rigidity that makes some proteins resistant to proteolytic cleavage, the SDS-resistant and non SDS-resistant proteins were subjected to a proteolytic susceptibility test using the non-specific and aggressive protease, proteinase K at the protease: protein ratio of 1:100. As shown in FIG. 5A, the SDS-resistant proteins remained largely intact after 48 hours of incubation with proteinase K at 25° C. Only TTR and SAP exhibited a small degree of degradation by proteinase K (FIG. 5). The remarkable degree of resistance to proteolysis exhibited by the kinetically stable/SDS-resistant proteins is uncommon among proteins and hints at the unusual degree of structural rigidity they posses. In contrast, of the 25 non SDS-resistant proteins studied, 18 were completely degraded and 7 proteins exhibited some degree of proteolytic resistance. A representative group (same as in FIG. 2B) is shown in FIG. 5B. These results show that whereas kinetically stable proteins are resistant to proteolytic cleavage, kinetic stability is not a requirement for proteolytic resistance. The different requirements for SDS- and protease-resistance may be due to the non-specific binding of SDS to unfolded proteins in contrast to the specific binding requirement of proteases. While a protease requires the binding of specific structural elements to its active site in order to initiate protein cleavage, SDS appears to only require access to the protein's interior. It has been shown that protease-resistance is influenced not only by the exposure of the unfolded chain, but also by sequence determinants within the unfolded protein that may caused these proteins to be poor substrates for proteolytic degradation (22). Thus, SDS-resistance is a much more effective probe for identifying proteins with high kinetic stability.

The results point to kinetic stability as the molecular basis for the resistance of some proteins to SDS. Since each of the SDS-resistant proteins studied was also found to be resistant to proteolysis by proteinase K, it is proposed that, like in the case of proteolytic susceptibility, resistance to SDS is linked to the reduced occurrence of both local and global unfolding transitions in these proteins. Like proteases, SDS binding appears to rely on transitions between protein conformations, moments of weakness in which the protein is susceptible to SDS binding, and thereby entrapment. Kinetically stable proteins are characterized by unusually low structural flexibility (12, 23). The structural rigidity of kinetically stable proteins results in suppression of partial unfolding. Furthermore, Truhlar et. al. have shown that it is not only the barrier towards global unfolding, but also the high cooperativity of the unfolding transition of kinetically stable proteins that results in its protease resistance (and presumably SDS resistance) by limiting partial unfolding transitions (24). Thus, this may explain why unless provided with energy in the form of heat (e.g. through boiling), kinetically stable proteins infrequently assume such open conformations under native conditions, and are therefore, resistant to SDS.

A key to understanding kinetic stability in proteins may lie in determining the physical basis for their structural rigidity, as this appears to be a common property of kinetically stable proteins (12, 23). Arguably, the most compelling evidence that rigidity may be the key physical requirement for protein kinetic stability comes from the observation that proteins become highly rigid and kinetically stable when incubated in very high concentrations of organic solvent (25, 26). In such an environment, the absence of bulk water presumably reduces the energetic driving force for partial and global unfolding, thereby increasing rigidity (26). Under normal aqueous environment, kinetically stable proteins may owe their rigidity to the lack of weak points on its surface where bulk water could penetrate to induce local and global unfolding. Consistent with this idea, recent work by Machius et. al. has shown that kinetic stability can be increased by introducing hydrophobic mutations at the surface of protein to stabilize and rigidify regions that may be involved in local unfolding (5). Furthermore, strategically located metal ions, disulfide bonds, salt-bridges, and hydrophobic residues at the surface, may be useful for enhancing the kinetic stability of a given protein by serving as molecular "clips" or "staples" to avoid water penetration, resulting in rigid structures where partially unfolded states are not sampled under native-like conditions.

Figure 6:
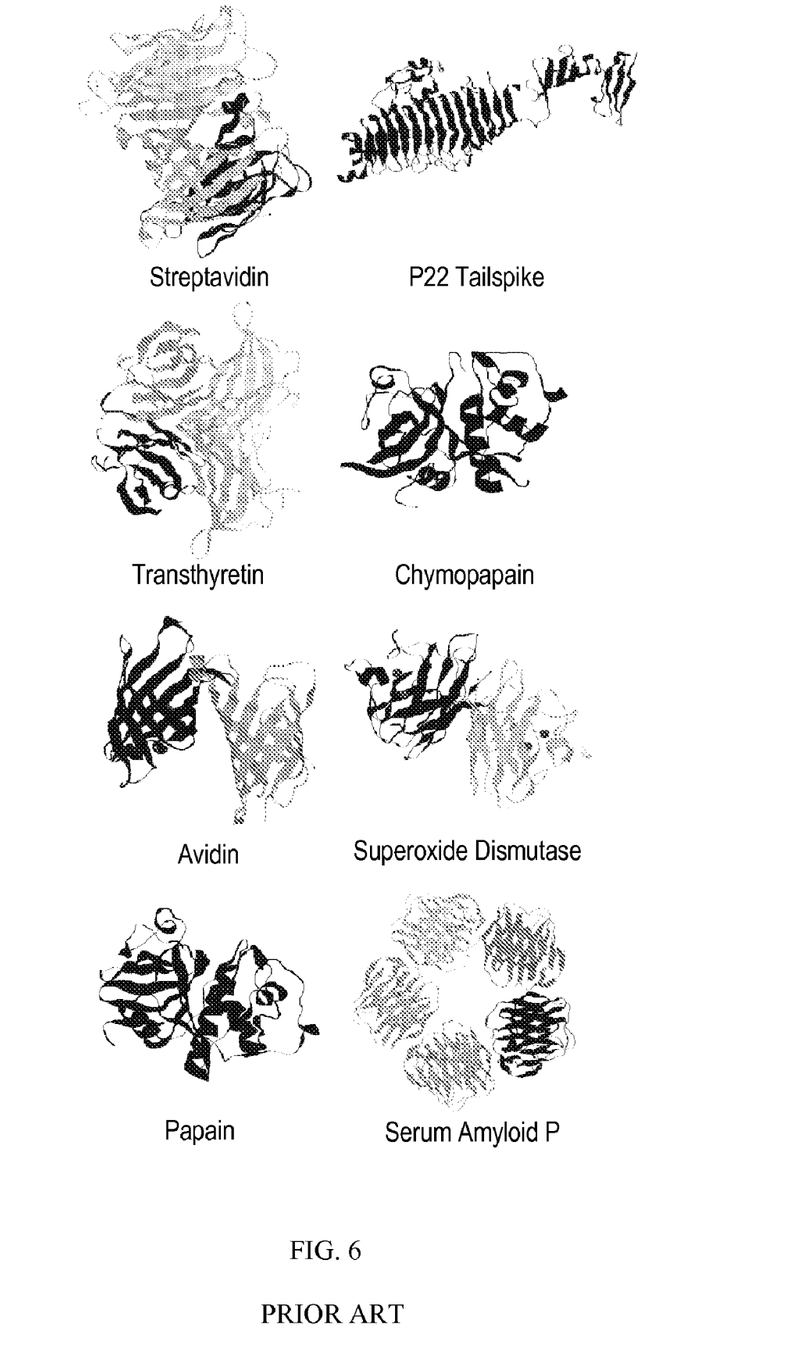
FIG. 6 are ribbon diagrams of the SDS-stable proteins revealing the high content of oligomeric β-sheet structure. Coordinates were obtained from the Protein Data Bank using the following PDB codes: SOD-1SPD; SVD-1SWU, TTR-1GKE, TSP-1TYU, CPAP-1YAL, PAP-1PPN, AVD-1RAV, SAP-1SAC.

In an attempt to better understand the structural basis for kinetic stability, a rudimentary structural analysis was performed on the pool of SDS-resistant proteins based on their structure coordinates obtained from the Protein Data Bank (PDB) (FIG. 6). Each protein was found to exhibit specific stabilizing characteristics, including disulfide bonds (PAP, CPAP, and SOD), oligomeric interfaces (all except PAP and CPAP), and bound metals (SOD). Amino acid composition calculations based on the PDB coordinates likewise yielded no common trend in the amino acid content and no consistent deviation from the amino acid composition found in natural proteins, implying that no correlation exists between kinetic stability and primary structure. However, the presence of predominantly β-sheet and oligomeric structure emerged as a common characteristic of most of the kinetically stable proteins studied. It is plausible that the higher content of non-local interactions in β-sheet proteins may allow for higher rigidity than in α-helical proteins. Although clearly not all oligomeric β-sheet proteins are kinetically stable/SDS-resistant (see Table 2), the apparent bias for kinetic stability in oligomeric β-sheet proteins may serve to prevent them from aggregation. When induced to assume an unfolded conformation, β-sheet proteins are particularly susceptible to misfolding and aggregation, potentially leading to protein misfolding diseases (18). It has been shown that to avoid aggregation natural β-sheet proteins use various negative design strategies, such as the placement of loops, β-bulges, prolines, and charged residues at the end of β-sheets (27). Perhaps kinetic stability may be another strategy used by nature to minimize the potential for protein misassembly. It will be interesting to determine how widespread this property is among other oligomeric and/or β-sheet proteins and whether it correlates with their tendency towards aggregation. Despite the apparent bias towards β-sheet proteins, the observation of kinetic stability and SDS-resistance in PAP and CPAP, which are monomeric proteins containing an α- and a β-domain, show that these properties are also accessible to other proteins.

In summary, the above results suggest that SDS resistance is a common property of kinetically stable proteins and that SDS-PAGE may be used as a simple assay to probe for kinetic stability in purified proteins or protein extracts. Without being limited to any scientific theory, the inventors believe that, analogous to proteolytic susceptibility, proteins become vulnerable to denaturation by SDS during their partial and global unfolding transitions. However, due to the non-specific nature of SDS denaturation, it is highly effective in detecting proteins that possess high kinetic stability. Together, these results provide compelling support to the idea that kinetic stability is a common property of rigid protein structures. The identification of a simple and effective assay for kinetic stability assay in accordance with the invention provides the opportunity to accumulate a larger database of kinetically stable proteins, thus paving the way for further studies geared towards understanding the relationship between kinetic stability and protein structure.

EXAMPLES

Example 1

SDS-polyacrylamide Gel Eectrophoresis (SDS-PAGE) Assay. Lyophilized proteins were obtained from Sigma (papain (PAP), chymopapain (CPAP), avidin (AVD), and superoxide dismutase (SOD)) and Calbiochem (streptavidin (SVD), serum amyloid P (SAP), and transthyretin (TTR)). *Salmonella* phage P22 tailspike (TSP) protein was a gift from J. King (MIT). All the remaining proteins (Table 2) were obtained from Sigma with the exception of catalase, which was purchased from Calbiochem. Stock solutions (1 mg/mL) of all proteins studied except papain, chymopapain, and P22 tailspike protein were made using 10 mM sodium phosphate buffer (pH 7.0) (PB). Stock solutions (1 mg/mL) of papain and chymopapain were prepared with 25 mM 2-amino-2-hydroxymethyl-1,3-propanediol (Tris), 1 mM EDTA (pH 5.3). The stock solution of the P22 tailspike protein was 0.8 mg/mL in 50 mM Tris, 2 mM EDTA (pH 7.6). All electrophoresis samples contained ~5 μg protein and 1% sodium dodecyl sulfate (SDS) in 0.125 M Tris (pH 6.8). Protein samples were unheated or boiled for 10 min. prior to analysis by SDS-polyacrylamide gel electrophoresis (SDS-PAGE), using 15% Acrylamide Pager Gold precast gels (Cambrex), and 0.1% SDS in Tris/Glycine buffer (pH 8.3) as running buffer. The gels were then stained using Coomassie Blue.

Example 2

Proteolysis. For limited proteolysis experiments the concentration of the proteins was determined by weighing the lyophilized protein on a microbalance. Each proteolysis reaction mixture contained about 0.5 mg/mL protein and 5 μg/mL proteinase K (Fisher Scientific) in 25 mM Tris, 1 μM EDTA (pH 8.3), and was incubated at 25° C. for 48 hours. The reaction was stopped with a solution of 2.5 μM phenylmethylsulfonyl fluoride, 4% SDS in 0.125 M Tris, 3.4 μM 1,4-Dithio-DL-threitol (pH 6.8)). Samples were boiled and gel electrophoresis was performed using 16% acrylamide Novex precast gels (Invitrogen). Running buffer was 0.1% SDS in Tris/Tricine buffer (pH 8.1).

Example 3

Fluorescence. Unfolding kinetics induced by guanidine hydrochloride (GdnHCl) were monitored using an F-4500 fluorescence spectrophotometer (Hitachi, Danbury, Conn.). The concentration of GdnHCl was determined using an Abbe Mark II refractometer (Leica, Buffalo, N.Y.). Protein solutions (0.05 mg/mL) in 25 mM PB, 0.20 M sodium chloride (pH 7.2) were treated with GdnHCl solution made using the same buffer to a final concentration of 6.6 M. The excitation/emission wavelengths used were: 275/350 nm (B2M), 275/360 nm (BLA, ConA, GAPDH, TIM), 280/320 nm (ADH), 295/360 nm (CPAP, TTR), 295/350 nm (PAP), 295/340 nm (SAP, TSP), 280/330 nm (SOD), 295/333 nm (SVD), and 280/340 nm (AVD). Kinetic traces were analyzed by fitting to a sum of exponentials.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

REFERENCES

1. Cunningham, E. L., Jaswal, S. S., Sohl, J. L., and Agard, D. A. (1999) Kinetic stability as a mechanism for protease longevity, *Proc. Natl. Acad. Sci. USA* 96, 11008-11014.
2. Ohnishi, S., and Kameyama, K. (2001) *Escherichia coli* OmpA retains a folded structure in the presence of sodium dodecyl sulfate due to a high kinetic barrier to unfolding, *Biochim. Biophys. Acta* 1515, 159-166.
3. Kaushik, J. K., Ogasahara, K., and Yutani, K. (2002) The unusually slow relaxation kinetics of the folding-unfolding of pyrrolidone carboxyl peptidase from a hyperthermophile, pyrococcus furiosus, *J. Mol. Biol.* 316, 991-1003.
4. Plaza del Pino, I. M., Ibarra-Molero, B., and Sanchez-Ruiz, J. M. (2000) Lower kinetic limit to protein thermal stability: a proposal regarding protein stability in vivo and its relation with misfolding diseases, *Proteins* 40, 58-70.
5. Machius, M., Declerck, N., Huber, R., and Wiegand, G. (2003) Kinetic stabilization of *Bacillus licheniformis* alpha-amylase through introduction of hydrophobic residues at the surface, *J. Biol. Chem.* 278, 11546-11553.
6. Mansfeld, J., Vriend, G., Dijkstra, B. W., Veltman, O. R., Van den Burg, B., Venema, G., Ulbrich-Hofmann, R., and Eijsink, G. H. (1997) Extreme stabilization of a thermolysin-like protease by an engineered disulfide bond, *J. Biol. Chem.* 272, 11152-11156.
7. Pozdnyakova, I., Guidry, J., and Wittung-Stafshede, P. (2001) Copper stabilizes azurin by decreasing the unfolding rate, *Arch. Biochem. Biophys.* 390, 146-148.
8. Rietveld, A. W., and Ferreira, S. T. (1998) Kinetics and energetics of subunit dissociation/unfolding of TIM: The importance of oligomerization for conformational persistence and chemical stability of proteins, *Biochemistry* 37, 933-937.
9. Solis-Mendiola, S., Gutierrez-Gonzalez, L. H., Arroyo-Reyna, A., Padilla-Zuniga, J., Rojo-Dominguez, A., and Hernandez-Arana, A. (1998) pH dependence of the activation parameters for chymopapain unfolding: influence of ion pairs on the kinetic stability of proteins, *Biochim. Biophys. Acta* 1388, 363-372.
10. Jaenicke, R., and Böjm, G. (1998) The stability of proteins in extreme environments, *Curr. Opin. Struct. Biol.* 8, 738-748.
11. Cavagnero, S., Debe, D. A., Zhou, Z. H., Adams, M. W. W., and Chan, S. I. (1998) Kinetic role of electrostatic interactions in the unfolding of hyperthermophilic and mesophilic rubredoxin, *Biochemistry* 37, 3369-3376.
12. Jaswal, S. S., Sohl, J. L., Davis, J. H., and Agard, D. A. (2002) Energetic landscape of α-lytic protease optimizes longevitiy through kinetic stability., *Nature* 415, 343-346.
13. Rupley, J. A. (1967) Susceptibility to attack by proteolytic enzymes, *Methods Enzymol.* 11, 905-917.
14. Kurzban, G. P., Bayer, E. A., Wilchek, M., and Horowitz, P. M. (1991) The quaternary structure of streptavidin in urea, *J. Biol. Chem.* 266, 14470-14477.
15. Colón, W., and Kelly, J. W. (1992) Partial denaturation of transthyretin is sufficient for amyloid fibril formation in vitro, *Biochemistry* 31, 8654-8660.
16. Chen, B.-l., and King, J. (1991) in *ACS Symposium Series* (Giorgiou, G., and Bernardez-Clark, E. d., Eds.) 119-132, American Chemical Society, Washington, D.C.
17. Lai, Z., McCulloch, J., Lashuel, H. A., and Kelly, J. W. (1997) Guanidine hydrochloride-induced denaturation and refolding of transthyretin exhibits a marked hysteresis: equilibria with high kinetic barriers, *Biochemistry* 36, 10230-10239.

18. Kelly, J. W. (1996) Alternative conformations of amyloidogenic proteins govern their behavior, *Curr. Opin. Struct. Biol.* 6, 11-17.
19. Reynold, J. A., Herbert, H., Polet, H., and Steinhardt, J. (1967) The binding of diverse detergent anions to bovine serum albumin, *Biochemistry* 6, 937-943.
20. Jones, M. N., Skinner, H. A., and Tipping, E. (1975) The interaction between bovine serum albumin and surfactants., *Biochem. J.* 147, 229-234.
21. Nelson, C. A. (1971) The binding of detergents to proteins, *J. Biol. Chem.* 246, 3895-3901.
22. Parsell, D. A., and Sauer, R. T. (1989) The structural stability of a protein is an important determinant of its proteolytic susceptibility in *Escherichia coli*, *J. Biol. Chem.* 264, 7590-7595.
23. Yuan, C., Li, J., Selby, T. L., Byeon, I.-J. L., and Tsai, M.-D. (1999) Tumor suppressor INK4: Comparisons of conformational properties between $p16^{INK4A}$ and $p18^{INK4C}$, *J. Mol. Biol.* 294, 201-211.
24. Truhlar, S. M., Cunningham, E. L., and Agard, D. A. (2004) The folding landscape of *Streptomyces griseus* protease B reveals the energetic costs and benefits associated with evolving kinetic stability., *Protein Sci.* 13, 381-390.
25. Zaks, A., and Klibanov, A. M. (1988) Enzymatic catalysis in nonaqueous solvents, *J. Biol. Chem.* 263, 3194-3201.
26. Partridge, J., Moore, B. D., and Halling, P. J. (1999) α-chymotrypsin stability in aqueous-acetonitrile mixtures: is the native enzyme thermodynamically or kinetically stable under low water conditions?, *J. Mol. Catal. B: Enzymatic* 6, 11-20.
27. Richardson, J. S., and Richardson, D. C. (2002) Natural beta-sheet proteins use negative design to avoid edge-to-edge aggregation, *Proc. Natl. Acad. Sci. USA* 99, 2754-2759.
28. Harushima, Y., Kuwajima, K., and Sugai, S. (1988) Hydrogen exchange of the tryptophan residues in bovine alpha-lactalbumin studied by UV spectroscopy, *Protein Sci.* 7, 1564-1574.
29. Corazza, A., Pettirossi, F., Viglino, P., Verdone, G., Garcia, J., Dumy, P., Giorgetti, S., Mangione, P., Raimondi, S., Stoppini, M., Bellotti, V., and Esposito, G. (2004) Properties of some variants of human beta2-microglobulin and amyloidogenesis., *J. Biol. Chem.* 279, 9176-9189.

What is claimed is:

1. A method of identifying the presence of kinetically stable proteins in a protein library comprising assaying the library for proteins that are resistant to denaturation by SDS and correlating said resistance to denaturation by SDS with the presence of kinetically stable proteins, wherein the assaying step comprises the steps of:
   a) providing at least one pair of substantially identical protein samples from the library;
   b) adding SDS to each sample of the pair of protein samples;
   c) boiling only one of the protein samples of the pair of protein samples;
   d) conducting SDS-polyacrylamide gel electrophoresis on the pair of protein samples;
   e) comparing the migration on the gel of proteins contained in the boiled protein sample to the migration on the gel of proteins contained in the unheated protein sample; and
   f) correlating proteins migrating slower in the unheated protein sample with resistance to denaturation by SDS.

2. A method according to claim 1 for identifying kinetically stable mutated proteins in a protein library of comprising the steps of:
   a) generating by site-directed mutagenesis, a library of mutated polynucleotides;
   b) expressing the library of mutated polynucleotides in host cells to obtain a library of mutated proteins; and
   c) screening the resulting library of mutated proteins for resistance to denaturation by SDS.

3. The method of claim 1 wherein the protein library is a library selected from the group consisting of known proteins, random proteins, mutagenized proteins, chimeric proteins, fusion proteins.

4. The method of claim 1 wherein the protein library is a library which results from rational protein design, site directed mutagenesis, directed evolution, protein genesis or gene shuffling.

5. A high-throughput screening assay for identifying the presence of kinetically stable proteins in a sample of proteins comprising the step of testing the sample for the presence proteins that are resistant SDS denaturation and correlating said protein resistance to denaturation by SDS with the presence of kinetically stable proteins, wherein the testing comprises the steps of:
   a) providing at least one pair of substantially identical protein samples, each sample comprising at least one protein in combination with SDS;
   b) boiling only one of the protein samples of the pair of protein samples;
   c) conducting SDS-polyacrylamide gel electrophoresis on the pair of protein samples;
   d) comparing the migration of proteins contained in the boiled protein sample to the migration of proteins contained in the unheated protein sample; and
   e) correlating proteins migrating slower in the unheated protein sample with resistance to denaturation by SDS.

6. A method for rapid screening of a protein library to identify kinetically stable proteins comprising the step of testing the protein library for proteins that are resistant to SDS denaturation and correlating said protein resistance to denaturation by SDS with identification of kinetically stable proteins in the library, wherein the testing step comprises the steps of:
   a) providing at least one pair of substantially identical protein samples derived from a protein library, each sample comprising at least one protein in combination with SDS;
   b) boiling only one of the protein samples of the pair of protein samples;
   c) conducting SDS-polyacrylamide gel electrophoresis on the pair of protein samples;
   d) comparing the migration of proteins contained in the boiled protein sample to the migration of proteins contained in the unheated protein sample; and
   e) correlating proteins migrating slower in the unheated protein sample with resistance to denaturation by SDS.

7. A method for rapidly identifying kinetically stable chimeric polypeptides present in a chimeric polypeptide library comprising the step of testing the chimeric polypeptide library for chimeric polypeptides that are resistant to SDS denaturation, wherein the testing step comprises the steps of:
   a) providing at least one pair of substantially identical chimeric polypeptide samples derived from a chimeric polypeptide library, each sample comprising at least one polypeptide in combination with SDS;
   b) boiling only one of the chimeric polypeptide samples of the pair of samples;
   c) conducting SDS-polyacrylamide gel electrophoresis on the pair of chimeric polypeptide samples; and d) comparing the migration of polypeptides contained in the boiled chimeric polypeptide sample to the migration of polypeptides contained in the unheated chimeric polypeptide sample.

8. A method of identifying the presence of kinetically stable proteins in a protein library comprising assaying the library for proteins that are resistant to denaturation by SDS wherein the assaying step is a fluorescence-based assay comprising the steps of:
   a) generating a library of proteins by a display methodology using a well plate format;
   b) contacting the library of displayed proteins with SDS;
   c) washing unbound SDS from the proteins;
   d) contacting the protein library with a fluorescent probe capable of binding to an SDS-protein complex;
   e) determining the intensity of fluorescence in each well; and
   f) correlating the lack of fluorescent intensity with resistance to denaturation by SDS; and correlating said resistance to denaturation by SDS with the presence of kinetically stable proteins.

9. The method of claim 8, wherein the display methodology is selected from the group consisting of phage display, yeast protein display, antibody display and bacterial display.

* * * * *